United States Patent [19]

Cingotti

[11] Patent Number: 5,427,800
[45] Date of Patent: Jun. 27, 1995

[54] PROCESS FOR PREPARATION OF AN EXTRACT OF ACTIVE INGREDIENTS IN A DRY ADSORBABLE FORM AND ADSORBABLE FORM AND ADSORBABLE MICROGRANULES THUS OBTAINED

[75] Inventor: Dominique Cingotti, Villeurbanne, France

[73] Assignee: Etablissements Rinrone, France

[21] Appl. No.: 963,818

[22] Filed: Oct. 20, 1992

[30] Foreign Application Priority Data

Oct. 24, 1991 [FR] France .................. 91 13355

[51] Int. Cl.⁶ .................. A61K 9/14; A61K 9/16; A61K 35/78
[52] U.S. Cl. .................. 424/489; 424/490; 424/491; 424/492; 424/493; 424/494; 424/495; 424/496; 424/497; 424/498; 428/404; 428/407; 427/212; 427/215; 427/220; 427/221
[58] Field of Search ............. 424/489, 490, 491, 492, 424/493, 494, 495, 496, 497, 498; 427/212, 215, 220, 221; 428/404, 407

[56] References Cited

U.S. PATENT DOCUMENTS

| | | | |
|---|---|---|---|
| 3,915,736 | 10/1975 | Oyamoda et al. | 427/212 |
| 4,447,349 | 5/1984 | Tai | 428/407 |
| 5,026,560 | 6/1991 | Mopino et al. | 424/490 |
| 5,158,779 | 10/1992 | Gergely et al. | 424/490 |

Primary Examiner—Thurman K. Page
Assistant Examiner—Peter F. Kulkosky
Attorney, Agent, or Firm—Harris Beach & Wilcox

[57] ABSTRACT

A process for the preparation of a dry adsorbable extract of at least one active ingredient, comprising the steps of: first, preparing an extract of the active ingredient in a solvent medium specific to the active ingredient; second coating granules of an absorbent carrier with the extract; third drying and calibrating to a predetermined size the coated granules; and finally absorbing the coated granules produced in step 3 in and on porous excipient nebulized microgranules, which have cavities and ducts which are partially filled by the coated granules, with a ratio of between 5 and 20 parts by weight of coated granules to 100 parts microgranules.

6 Claims, No Drawings 5,427,800

PROCESS FOR PREPARATION OF AN EXTRACT OF ACTIVE INGREDIENTS IN A DRY ADSORBABLE FORM AND ADSORBABLE FORM AND ADSORBABLE MICROGRANULES THUS OBTAINED

BACKGROUND OF THE INVENTION

The invention concerns a new process for the preparation of an extract of active ingredients in a dry ingestible per-os form, particularly of vegetable, animal or other origin; it also concerns the porous adsorbable microgranules of this type that are prepared.

Preparing extracts of active ingredients is well known, for example of natural origin, particularly in the form of solutions, of macerations or of tinctures. Administering these extracts in dry form requires dosages that are precise and thus difficult to reproduce.

Currently, in order to obtain such dry extracts, processes are made which use a significant heat supply, such as nebulizing, roller dryers, evaporation under vaccum. If the type of compounds so obtained are easily administered by mouth (per-os), on the other hand, all the preparation processes that use an increase in temperature alter the active ingredients of the extracts and modify their stability, particularly because of hygroscopic regain and lumpiness, which leads to difficult handling.

The invention provides a process which permits administering the active ingredients in solid form, which is easier to control and easier to reproduce. It also provides a process which permits selecting the active ingredients used, while assuring a certain stability over time without thermal deterioration.

The invention remedies these inconveniencies. It provides a process that is easy to use, permits obtaining dry adsorbable per-os extracts that contain a large percentage of active ingredients and are stable over time.

SUMMARY OF THE INVENTION

This process for preparation of an extract of active ingredients in dry ingestible per-os form comprises the steps of:
first, preparing an extract of active ingredients in a solvent medium specific to the respective active ingredients;
then, depositing this extract on granules of an adsorbent carrier;
then, gauging and drying the granules coated in the manner;
finally, adsorbing these coated granules in and on porous microgranules of nebulized excipient, presenting cavities and ducts, in a ratio of 5 to 20% by weight, to the weight of the said microgranules, in such a way as to fill part of the cavities and the ducts.

In other words, the invention consists during a first phase in depositing the extract of the active ingredients of vegetable, animal or other origin on the porous granules; then, in a second phase, in having these coated granules adsorbed on porous nebulized microgranules of excipient, of which the cavities and the ducts are in part essentially filled by the coated granules. In this way, oral microgranules are obtained that include active ingredients that are stable and easily adsorbable per-os.

DETAILED DESCRIPTION OF THE INVENTION

In the description and in the claims, the phrase "extract of active ingredients in a solvent medium specific to the named active ingredients" should be understood as any form of solution containing the active ingredients of vegetable, animal or other origin, such as solutions, macerations, tinctures. These extracts are prepared in a known manner, particularly in a solvent medium appropriate to the active ingredients involved. Very generally speaking, ethanol is used. Any vegetable (or other) extracts for internal usage (by mouth), pharmaceutical or other usage, can be used with a non-thermolabile process. Very generally speaking, the extract contains from 1 to 3% and preferably 2% of dry products of the active ingredients.

As a function of the active ingredients involved, the solvent medium used is either water or, still better, an alcohol medium, even hydroalcohol. It is important that the alcohol solvent is non-toxic and has a low vapor tension. In practice, ethanol is used.

Once this extract of active ingredients is prepared in a known manner, it is deposited, particularly by moistening, by vaporizing . . . on compatible adsorbent carrier granules, such as porous colloidal or precipitated silica, even on microcrystalline cellulose, having a surface area between ten and three hundred square meters per gram. These porous granules are well known and widely used, such that it is not useful to describe them in detail here. As already mentioned, it is important that the surface area of the granules is between ten and three hundred square meters per gram. Microcrystalline cellulose can also be used as an adsorbent carrier other than silica, particularly when the final application planned is homeopathic.

The coating preferably takes place at ambient temperature in a planetary mixer, with slight agitation. First, the granules are placed in the mixer and are then moistened with the extract, in a ratio on one volume per one half to three volumes. In fact, if the volume of the extract exceeds twice the mass of the granules, a gel is obtained that is difficult to dry and to handle. Still it has been observed that if the quantity of granules exceeds three times the extract volume, a wetting heterogeneity is rapidly obtained.

Once the granules are coated, these granules are gauged by passing them through a screen, of which the mesh of between one and two millimeters, in such a way as to obtain perfectly homogeneous granules. It is advantageous to use mechanical gauging on an oscillating screen. The the screened coated granules are dried in a slightly ventilated atmosphere, for example at 40° C., with recycling and recuperation of the solvent. Once the drying is completed, there is a repeat gauging on a smaller screen, for example 0.5 millimeter/gauge.

Once the coated granules are gauged, these impregnated granules are adsorbed on and in nebulized porous excipient microgranules that are standard in the pharmaceutical industry. These nebulized porous microgranules of excipient are well-known and do not need to be described in detail here. These microgranules are obtained by a spray-drying process by means of a "nebulizer", also known as an "atomizer" or as a "spray drier". These microgranules are advantageously excipient of -ose compounds. As it is known, there porous nebulized microgranules present a multitude of superficial cavities and internal ducts, i.e. small radial ducts that point towards the interior of the granules. In practice, these microgranules have a dimension between 0.1 and 1 millimeter, preferably in the area of 0.5 millimeter. It then follows that the coated granules of silica or of microcrystalline cellulose, of which the size is on the order of one micron, will lodge easily in the superficial cavities as well as in the ducts, and remain trapped there. Advantageously, sorbitol granules can be used, namely those sold by MERCK under the brand name SORBITOL INSTANT.

Advantageously, the quantity of coated granules represents from 5 to 20%, preferably 10%, of the weight of the excipient in the form of microgranules. It has been observed that if the proportion of the granules is less than 5%, a heterogeneous mixture was obtained. On the other hand, if this percentage exceeds 20%, a saturation is rapidly obtained with phase shift between the fine phase and the coarse phase and the cost of the operation is disadvantageously increased. As already mentioned, excellent results are obtained with a ratio in the area of 10%.

The -ose compounds, which are easily used, are preferably used as microgranules, such as sorbitol and mannitol compounds obtained by nebulizing. It is important that this carrier has a strong adsorption capacity to retain the active substances and permit obtaining a supersaturated structure of granules coated by filling the reticulated system. This also permits obtaining specific final forms by direct compression.

The mixture of microgranules and coated granules is made in a known manner, particularly in a mixer at ambient temperature.

In this way, oral adsorbable excipient microgranules are obtained that have cavities and ducts which are characterized by the fact that the said cavities and the said ducts are filled with granules, for example of colloidal silica, coated with an active extract, particularly vegetable.

EXAMPLES

Example 1

In a known manner, an alcoholic tincture of passiflora is prepared by maceration during forty five days at ambient temperature, using the above ground parts of the plant in ethanol at 90°. After maceration, the tincture obtained is drawn off, dried, then filtered. This tincture contains about 0.2% flavanoids.

This tincture is then atomized at ambient temperature on granules of precipitated colloidal silica, marketed by DEGUSSA under the name FK 320 DS, presenting a surface area of one hundred and seventy (170) $m^2$/gram, an average primary particle size of eighteen nanometers, a pH value of 6.3 and a density (packed, but not compressed) of 220. One volume of tincture is mixed for a part of silica granules. These wetted silica granules are agitated for five to fifteen minutes at ambient temperature in such a way as to obtain a homogeneous wetting. A fine powder, lightly wetted of dark green color like chlorophyll is thus obtained.

The coated granules are then gauged by passage over an oscillating screen, of which the size if between 1.5 and 2 millimeters. Drying is in a thin layer for four hours at about 40° C. in a ventilated atmosphere. Gauging is performed again on an oscillating screen on which the size is reduced to 0.5 millimeters.

The silica granules thus coated can easily be stored.

Ninety volumes of sorbitol nebulized microgranules, marketed by MERCK A. G. under the name SORBITOL INSTANT PHARMA 3140, supplied in the form of fine white odorless crystalline powder, presenting a multitude of surface cavities and radial ducts, are placed in a planetary mixer. This compound presents an average granulation comprising a particle size of between 210 and 500 micrometers (microns) for between 60 to 70% and between 500 and 850 micrometers for between 25 to 35% of the particles.

Still at ambient temperature, ten volumes of the above coated silica granules are placed in the mixer containing the nebulized microgranules. Then agitation occurs for about twenty minutes to homogenize.

Microgranules of sorbitol are thus obtained, of which the cavities and the ducts are filled with silica granules coated with dry extracts bearing the active ingredients of the passiflora.

Using these microgranules, capsules are packaged of two hundred fifty milligrams which are administered per-os on request as a tranquilizer, using nine capsules per day and without familiarization. In this way, a supersaturated mixture is obtained that has:
- excellent direct compressibility;
- excellent binding capacity with the active ingredients;
- good miscibility with the active ingredients adsorbed on the intermediate phase with the carrier because of the low bulk density;
- good regulated stability, with neither the risk of phase shift nor of "flaking off" of the sorbitol carrier.

Example 2

Example 1 is repeated, using not an alcoholic tincture of passiflora, but a multi-vegetable extract in ethanol at 60° C., intended for venous circulation, containing a mixture of equal proportions of hawthorn, olive and garlic. The same proportions and the same components are used as in Example 1.

Microgranules are thus obtained that are of whitish-gray color, easy to administer in per-os form of two hundred fifty milligram capsules in nutritive gelatin, six capsules a day for twenty to thirty days.

Example 3

Example 2 is repeated with extracts of harpogophytum root, of orthosiphon, of fumitory and of camomile in equal proportions in 60% ethanol.

As above, in this way adsorbed microgranules are obtained that are easy to package in the form of two hundred fifty milligram capsules. These capsules are effective in the treatment of hepatic disturbances by administering per-os two to six capsules a day for twenty to thirty days.

Example 4

The silica granules in the preceding examples are replaced by porous granules of nebulized microcrystalline cellulose marketed by DEGUSSA, under the name ELCEMA P 050, having a particle of which size is between 40 and 70 microns and a bulk density of 230 g/liter.

Using the procedure as in example 1, two volumes of these granules are wetted in a volume of homeopathic dilution (i.e. the Hahnemann centesimal dilution).

As a function of the standard homepathic dose, between 80 and 97% of the same reticular sorbitol microgranules is mixed in with between 13 and 20% of the microcrystalline cellulose microgranules referenced above. These sorbitol granules may be in the form of a capsule containing granules, 3 to 5 granules, a tube containing pellets, or drops for drinking (in the amount of 15 drops).

The mixture thus obtained may be dispensed in various per-os forms, such as capsules, tablets that are advantageously obtained by direct compression without additive, or packets that are easily soluble in water.

Example 5

Example 1 is repeated, but with direct impregnation of the sorbitol microgranules with the hydroalcoholic solution, without using the intermediary step of silica granules.

A congealed mass is rapidly obtained that is impossible to homogenize, dry and gauge.

The process according to the invention presents a number of advantages in comparison to those currently marketed. The following can be named:
- the possibility of presenting an active liquid extract in dry form that is easy to administer by mouth in a precise and reproducible manner, which guarantees the entirety;
- the simplicity of use;
- the ease of oral adsorption since the excipient base masks the taste of the tincture, thus improvement of the organoleptic and gustatory character of the compound administered;
- the ease of compression or administering these extracts in the form of capsules.

In this manner, this process may be used advantageously for all extracts intended to be administered by mouth (per-os) in the form of tablets, of capsules, lozenges to such on; particularly of vegetable, mineral, animal or even of the active ingredients, with semi-synthesis or total synthesis for pharmaceutical, dietary, nutrutive or other use.

What is claimed is:

1. A process for the preparation of a dry adsorbable extract ingestible per-os of at least one active ingredient, comprising the steps of:
   1) first, preparing an extract of said active ingredient in a solvent medium said solvent medium comprising at least one solvent selected from the group consisting of alcohol and water;
   2) second, coating granules of an absorbent carrier with said extract, said carrier granules being selected from a group comprising porous silica and microcrystalline cellulose, and presenting a surface area of between 10 and 300 square meters per gram;
   3) third, drying said coated granules and gauging said coated granules to a predetermined size; and
   4) finally, absorbing the dried and gauged coated granules inside of and on the surface of porous microgranules of nebulized excipient of -ose compounds, said microgranules having a dimension of between 0.1 and 1 mm and having cavities and ducts which are partially filled by said coated granules, to yield a preparation having a ratio of between 5 and 20 parts by weight of coated granules to 100 parts of microgranules.

2. The process of claim 1, wherein the extract of active ingredient is sprayed on said absorbent carrier granules at ambient temperature, in a ratio of two volumes of extract for one half to three volumes of absorbent carrier granules and simultaneously agitating said sprayed granules.

3. The process of claim 2 wherein the extract is an extract of one of the group of plants and animals and contains between one and three percent of the active ingredient.

4. The process of claim 1 wherein the gauging and drying of said coated granules is accomplished by the steps of passing said coated granules over a first oscillating screen said first screen having a mesh opening of two millimeters; drying said coated granules in a ventilated atmosphere at 40° C.; and passing said dried granules over a second oscillating screen, said second screen have a mesh opening smaller than that of the first screen.

5. The process of claim 1 wherein said absorbent granules are sorbitol.

6. Porous nebulized microgranules of ose compound pharmaceutical excipient, and said microganules having a dimension of between 0.1 and 1 mm, which are ingestable per os, and which have cavities and ducts, said cavities and ducts being at least partially filled with absorbent granules selected from a group comprising porous silica and microcrystalline cellulose and presenting a surface area of between 10 and 300 square meters per gram, wherein said absorbent granules are coated with an extract of at least one active ingredient.

* * * * *

UNITED STATES PATENT AND TRADEMARK OFFICE
CERTIFICATE OF CORRECTION

PATENT NO. : 5,427,800
DATED : June 27, 1995
INVENTOR(S) : Dominique Cingotti

It is certified that error appears in the above—identified patent and that said Letters Patent is hereby corrected as shown below:

On the title page, item [73] please delete "France" and insert --Liechtenstein--.

Signed and Sealed this

Twenty-ninth Day of July, 1997

Attest:

BRUCE LEHMAN

Attesting Officer  Commissioner of Patents and Trademarks